United States Patent
Baumann et al.

[11] Patent Number: 6,008,309
[45] Date of Patent: Dec. 28, 1999

[54] MESOSCOPIC ORGANOPOLYSILOXANE PARTICLES WITH CHEMICALLY BOUND METALLIC COMPOUNDS

[75] Inventors: Frank Baumann, Mehring; Bernward Deubzer; Geck Michael, both of Burghausen; Schmidt Manfred, Bodenheim, all of Germany

[73] Assignee: Wacker-Chemie GmbH, Munchen, Germany

[21] Appl. No.: 09/043,136

[22] PCT Filed: Sep. 26, 1996

[86] PCT No.: PCT/EP96/04209

§ 371 Date: Mar. 9, 1998

§ 102(e) Date: Mar. 9, 1998

[87] PCT Pub. No.: WO97/11984

PCT Pub. Date: Apr. 3, 1997

[30] Foreign Application Priority Data

Sep. 28, 1995 [DE] Germany ............... 195 36 182

[51] Int. Cl.⁶ .................................... C08G 79/00
[52] U.S. Cl. .................... 528/9; 528/14; 528/15; 528/17; 528/18; 528/19; 526/93; 526/117; 526/113; 526/126
[58] Field of Search .................. 528/15, 9, 18, 528/17, 14, 19; 526/126, 117, 113, 93

[56] References Cited

U.S. PATENT DOCUMENTS 5,187,134 2/1993 Panster et al. .
5,241,036 8/1993 Hsiue et al. ..................... 525/479
5,442,025 8/1995 Spes et al. ...................... 528/15

FOREIGN PATENT DOCUMENTS 0638604 2/1995 European Pat. Off. .
0744432 11/1996 European Pat. Off. .

OTHER PUBLICATIONS

R. H. Grubbs, Chemtech, Aug. 1977, p. 512 et seq.
D. D. Whitehurst, Chemtech, Jan. 1980, p. 44 et seg.
Derwent Abstract corresponding to DE–C 3029599 (#82–11871E).
Derwent Absract corresponding to DE–C 3925359 (#91–037961).
M. Schmidt "Simultaneous Static and Dynamic Light Scattering: Applications to Polymer Structure Analysis", contained in: Dynamic Light Scattering: The Method and Some Applications, Brown, W. (Editor), Oxford University Press, Oxford, UK, 372–406 (1993).
Antonietti (Angew. Chemie 100 (1998) 1813–1817).
Derwent Abstract corresponding to EP 0638604 (#95–076322).
Derwent Abstract corresponding to EP 0744 432(#97–001220).

*Primary Examiner*—Melvyn I. Marquis
*Attorney, Agent, or Firm*—Brooks & Kushman P.C.

[57] ABSTRACT

Organopolysiloxane particles useful as catalysts, are cross-linked, comprise a single molecule, have chemically bound metallic compounds and an average diameter of from 5 to 200 nm and are soluble in at least one solvent chosen from dichloromethane, pentane, acetone, ethanol and water to at least 1% by weight. At least 80% of the particles have a diameter which deviates a maximum of 30% from the average diameter.

17 Claims, No Drawings

MESOSCOPIC ORGANOPOLYSILOXANE PARTICLES WITH CHEMICALLY BOUND METALLIC COMPOUNDS

The invention relates to monodisperse soluble organopolysiloxane particles which comprise a single molecule and carry chemically bonded metal compounds, and to their preparation and use. The organopolysiloxane particles have an average diameter of 5 to 200 nm and are therefore in the mesoscopic size range.

In homogeneously catalyzed reactions with known homogeneous catalysts, a reaction product which is solid or insoluble in the reaction medium may be deposited on the internal wall of the reactor during continuous operation. This process, called fouling, usually leads to an interruption in operation.

Complexing ligands fixed to organic supports, such as polystyrene, and inorganic supports, such as silica gel, and the metal complexes which can be prepared with these are described comprehensively in R. H. Grubbs, CHEMTECH, August 1977, page 512 et seq. and D. D. Whitehurst, CHEMTECH, January 1980, page 44 et seq. The aim of heterogenization of the catalytically active metal complexes here is to avoid the disadvantages of homogeneous catalysis and to combine the advantages of homogeneous catalysts, i.e. high selectivity and activity, with the advantages of heterogeneous catalysts, i.e. easy removal and recovery of the catalyst from a liquid reaction mixture and no fouling in the case of solid reaction products.

The silicon dioxide-based inorganic support materials used to date, such as pyrogenic silicic acid or ground and, where appropriate, thermally modified silica gels, have non-uniform particle size distributions and particle sizes from 0.001 mm to 3 mm. Another disadvantage of these support materials is their irregular particle structure and the restriction to a low metal complex density on the support surface. These particles are insoluble in organic solvents.

Processes based on the sol-gel process for the preparation of spherical silica gel particles having a particle diameter of 0.01 mm to 3 mm and a relatively freely adjustable covering density of the silica support with the catalytically active metal complex compound by cocondensation of amine- and phosphine-functionalized trialkoxysilanes, preferably with tetraethoxysilane, are described in DE-C 30 29 599 and DE-C 39 25 359, as well as in U.S. Pat. No. 5,187,134. The resulting catalyst systems are insoluble in all solvents.

The object was to provide soluble organopolysiloxane particles which carry chemically bonded metal compounds and have a monodisperse particle size distribution within a size range from 5 to 200 nm.

The invention relates to crosslinked organopolysiloxane particles which comprise a single molecule, carry chemically bonded metal compounds, have an average diameter of 5 to 200 nm and are soluble to the extent of at least 1% by weight in at least one of the solvents chosen from the group consisting of methylene chloride, pentane, acetone, ethanol and water, at least 80% of the particles having a diameter which deviates not more than 30% from the average diameter.

The organopolysiloxane particles typically have average molecular weights of at least $10^5$, in particular $5 \times 10^5$, and preferably not more than $10^{10}$ g/mol, in particular $10^9$. The average diameters of the organopolysiloxane particles are preferably at least 10 and not more than 150 nm. Preferably, at least 80% of the particles have a diameter which deviates not more than 20%, in particular not more than 10%, from the average diameter. The organopolysiloxane particles are preferably spherical particles.

The organopolysiloxane particles are soluble in solvents and can therefore be employed as homogeneous catalysts, although the catalytically active complex is immobilized on the mesoscopic support system. Preferably, the solubility in a solvent is at least 2% by weight, in particular 10% by weight. The solvent in which the organopolysiloxane particles dissolve depends on the build-up of the organopolysiloxane particles, and in particular on the groups on the surface of the organopolysiloxane particles. There is a suitable solvent for all organopolysiloxane particles. Examples of such solvents are water; alcohols, such as methanol, ethanol, n-propanol and iso-propanol; ethers, such as dioxane, tetrahydrofuran, diethyl ether and diethylene glycol dimethyl ether; chlorinated hydrocarbons, such as methylene chloride, chloroform, carbon tetrachloride, 1,2-dichloroethane and trichloroethylene; hydrocarbons, such as pentane, n-hexane, cyclohexane, hexane isomer mixtures, heptane, octane, wash benzine, petroleum ether, benzene, toluene and xylenes; ketones, such as acetone, methyl ethyl ketone and methyl isobutyl ketone; dimethylformamide, carbon disulfide and nitrobenzene, or mixtures of these solvents, as well as monomers, such as methyl methacrylate or styrene, and polymers, such as liquid organopolysiloxanes.

The number of chemically bonded metal compounds per organopolysiloxane particles is at least 1, preferably at least 10, in particular at least 100, and preferably not more than $10^6$, in particular not more than $10^5$, more preferably not more than $10^4$. The number of metal compounds can be determined by spectroscopic methods, such as UV-Vis.

The metal compounds which are bonded chemically to the organopolysiloxane particles are preferably chosen from the group consisting of metal compounds of main groups II, III, IV and V and the subgroups of the Periodic Table of the Elements, in particular metal compounds of subgroup I, IV, VI, VII and VIII.

The metal compounds are preferably coordinately bonded to the surface of the organopolysiloxane particles, and they are then complex compounds, where the metal atom of a metal compound can be bonded to one or more organopolysiloxane particles. A metal atom of a metal compound can be bonded coordinately to the same organopolysiloxane particle via one or more ligands. The ligands to which the metal compounds are bonded coordinately can be bonded directly to a silicon atom on the surface of the organopolysiloxane particles or be attached via a spacer, i.e. a divalent organic radical, to a silicon atom. In addition to the organopolysiloxane particles bonded coordinately via ligands, the metal compound can also have low molecular weight ligands to satisfy any free coordination sites still present, and/or, where appropriate, counter-ions for charge compensation.

Particularly preferred organopolysiloxane particles have, on the surface, units which are chosen from units of the general formulae $$[AR_2SiO_{1/2}] \tag{1}$$

$$[ARSiO_{2/2}] \tag{2}$$ and $$[ASiO_{3/2}] \tag{3},$$

and the remaining units of the organopolysiloxane particles comprise 0.5 to 80.0% by weight of units of the general formula $$[R_3SiO_{1/2}] \tag{4},$$

0 to 99.0% by weight of units of the general formula $$[R_2SiO_{2/2}] \quad (5),$$

0 to 99.5% by weight of units of the general formula $$[RSiO_{3/2}] \quad (6) \text{ and}$$

0 to 80.0% by weight of units of the general formula $$[SiO_{4/2}] \quad (7),$$

in which

A is a ligand unit of the general formula $$spL' \quad (8) \text{ or}$$

$$spsp'L'' \quad (9)$$

at least one unit of the general formulae (8) or (9) per organopolysiloxane particle being bonded in a complex of the general formulae $$spL''_iML_k \quad (10) \text{ or}$$

$$spsp'L''_iML_k \quad (11)$$

and in which

M is a metal of subgroup I, IV, VI, VII or VIII of the Periodic Table of the Elements, L is a complexing ligand in the coordination sphere of the metal M, L' is a complexing ligand in the coordination sphere of the metal M bonded via a spacer sp to the surface of an organopolysiloxane particle, L'' is a complexing ligand in the coordination sphere of the metal M bonded via two spacers sp and sp' to the surface of an organopolysiloxane particle, sp and sp' are identical or different bivalent SiC-bonded, optionally substituted $C_0$- to $C_{18}$-hydrocarbon radicals, which can be interrupted by divalent radicals, bonded to carbon atoms on both sides, from the group consisting of —O—, —COO—, —OOC—, —CONR$^2$—, —NR$^2$CO—, —CO— and —[SiR$_2$]$_1$—, R is identical or different monovalent SiC-bonded, optionally halogen-substituted $C_1$- to $C_{18}$-alkyl radicals, i has values from 1 to not more than the coordination number of the metal M, k has values from 0 to not more than the coordination number of the metal M minus i and l has values from 1 to 100.

The complexing ligand L preferably has a molecular weight of not more than 500, in particular not more than 200 g/mol. Examples of complexing ligands L are carbon monoxide, nitrogen oxide, trialkylphosphines, alkylarylphosphines, triphenylphosphine, tetraphenyldiphosphines bridged by hydrocarbon radicals having 1 to 6 carbon atoms, phosphite, triphenylarsine, trialkoxyphosphines, sulfonated phosphanes, carboxylated phosphanes, phosphanes with quaternized aminoalkyl and aminoaryl substituents, phosphanes with hydroxyalkyl and polyether substituents, phosphinoalkylphosphonium salts, a secondary or tertiary alkylamine with linear or branched alkyl groups containing 1 to 10 C atoms, secondary or tertiary diamines, which may be bridged by 1 to 6 C atoms, benzylamine, dialkyl sulfide, olefins, diolefins, cyclic olefins having 4 to 30 C atoms, cyclic diolefins, such as cyclooctadiene, having 4 to 30 C atoms, cyclic aromatic compounds, such as the cyclopentadienyl ring, having 5 to 30 C atoms, alkynes, nitrile, isonitrile, cyanate, isocyanate and solvents, such as water, ether and alcohols.

Any charge compensation which may be necessary is carried out in the case of all the organopolysiloxane particles according to the invention with inorganic or organic anions, such as the chloride, bromide, iodide, nitrate, sulfate, phosphate, acetylacetonate, acetate, trifluoroacetate, trichloroacetate, propionate, methylate, ethylate, propylate, butylate, phenylate, methylaluminumoxylate, perchlorate, tetraphenylborate, hexafluorophosphate, methyl, ethyl, propyl, butyl, phenyl or perfluorophenyl ion, if appropriate with complete or partial replacement of such anions by hydride ions.

Examples of complexing ligands L' are linear and cyclic alkenyl radicals having up to 30 C atoms, such as the vinyl, allyl, n-5-hexenyl, 4-vinylcyclohexyl and 3-norbornenyl radical; linear and cyclic alkenedienyl radicals having up to 30 C atoms, such as the butadienyl, cyclopentadienyl and cyclooctadienyl radical; aryl radicals having up to 30 C atoms, such as the fluorenyl and indenyl radical; heterocyclic radicals having up to 30 C atoms which contain one or more identical or different heteroatoms, such as nitrogen, oxygen or sulfur atoms, such as pyridine derivatives, bipyridine derivatives, imidazole derivatives, thiophene derivatives and furan derivatives; mercaptoalkyl radicals having 2 to 20 C atoms, thioalkyl radicals having 2 to 20 C atoms, cyanoalkyl radicals having 2 to 20 C atoms, secondary and tertiary aminoalkyl radicals having 2 to 30 C atoms, secondary and tertiary diamino radicals having 2 to 30 C atoms, secondary and tertiary aminoaryl radicals having 6 to 30 C atoms, acyloxyalkyl radicals having 2 to 30 C atoms, hydroxyalkyl radicals having up to 30 C atoms, phosphinoalkyl radicals having up to 30 C atoms, diphosphinoalkyl radicals having up to 30 C atoms, phosphinoaryl radicals having 6 to 30 C atoms, phosphinoalkylaryl radicals having 6 to 30 C atoms, urea derivatives having up to 30 C atoms, thiourea derivatives having up to 30 C atoms and 1,3-diketones having up to 30 C atoms.

Preferred complexing ligands L' are unsubstituted and substituted $C_2$- to $C_6$-alkyl radicals, in particular the 3-mercaptoalkylpropyl, 3-aminopropyl, (2-aminoethyl)-3-aminopropyl, (3-dialkylphosphino)- and (3-alkylarylphosphino)propyl radical; $C_2$- to $C_8$-alkenyl radicals, in particular the vinyl and allyl radical; $C_4$- to $C_{20}$-alkyldienyl radicals, in particular the cyclopentadienyl and cyclooctadienyl radical; $C_6$- to $C_{20}$-aryl radicals, in particular the indenyl and fluorenyl radical and indenyl-cyclopentadienyl, fluorenyl-cyclopentadienyl, indenyl-indenyl and fluorenyl-fluorenyl radicals bridged via —CR$_2^2$—, —(CH$_2$)$_n$— or —SiR$_2^2$— in which R$^2$ and n have the above meanings; and $C_4$- to $C_{10}$-heterocycle radicals, in particular the pyridine and bipyridine radical.

Examples of the divalent complexing ligands L'' are the groups —N=N—, —N=N=NR$^2$—, —NR$^2$—, —NR$^2$—CO—NR$^2$—, —NR$^2$—CS—NR$^2$—, —[NR$^2$—(CH$_2$)$_n$]$_m$—, —O—O—, —CO—CO—, —CO—CH$_2$—CO—, —[O—(CH$_2$)$_n$]$_m$—, —Sx—, —PR$^2$— and [—PR$^2$—(CH$_2$)$_n$)$_m$—, in which R$^2$ is a hydrogen atom or a radical R, m has the values 1, 2, 3 or 4, n has the values 1, 2, 3 or 4 and x has the values 1, 2, 3 or 4.

Further examples of the complexing ligands L'' are the examples listed for complexing ligands L', which then have two bonding sites for the spacers sp and sp'.

Preferred divalent complexing ligands L" are —NR²—, —[NR²—(CH₂)₂]₂—, —PR²—and [PR²—(CH₂)₂]₂—, in particular —NR²— and —PR²—, in which R² is an unsubstituted $C_1$- to $C_6$-alkyl radical.

The carbon atoms on the complexing ligands L, L' and L" can be substituted, for example by halogen atoms, such as fluorine, chlorine or bromine atoms, and cyano groups.

The complexing ligands L, L' and L" can be sterically bulky and/or chiral, and the complex as a result also becomes sterically bulky and can be employed, for example, for stereoselective reactions.

Examples of the divalent radicals sp and sp' are saturated alkylene radicals, such as the methylene and ethylene radical, as well as propylene, butylene, pentylene, hexylene, cyclohexylene and octadecylene radicals or unsaturated alkylene or arylene radicals, such as the hexenylene radical and phenylene radicals, and polyoxyalkylene radicals.

Preferred radicals sp and sp' are saturated alkylene radicals having 1 to 10 C atoms, in particular the methylene, ethylene and propylene radical.

Examples of unsubstituted radicals R are alkyl radicals, such as the methyl, ethyl, n-propyl, isopropyl, n-butyl, iso-butyl, tert-butyl, n-pentyl, isopentyl, neo-pentyl and tert-pentyl radical, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, decyl radicals, such as the n-decyl radical, dodecyl radicals, such as the n-dodecyl radical, and octadecyl radicals, such as the n-octadecyl radical; and cycloalkyl radicals, such as cyclopentyl, cyclohexyl, 4-ethylcyclohexyl and cycloheptyl radicals, norbornyl radicals and methylcyclohexyl radicals. Examples of halogen-substituted alkyl radicals as the radical R are the chloromethyl, 3-chloropropyl, 3-bromopropyl, 3,3,3-trifluoropropyl and 5,5,5,4,4,3,3-heptafluoropentyl radical.

The radical R is preferably unsubstituted $C_1$- to $C_6$-alkyl radicals, phenyl radicals and hydrogen, in particular the methyl radical.

Preferably, independently of one another, i has the values 1, 2 or 3, in particular 1, k has the values 1, 2, 3 or 4 and l has the values from 2 to 20.

The organopolysiloxane particles preferably comprise at least a total of 0.1% by weight of units of the general formula (1) to (3), and the remaining units of the organopolysiloxane particles comprise 1 to 80.0% by weight of units of the general formula (4), 0 to 98.0% by weight of units of the general formula (5), 0 to 99.0% by weight of units of the general formula (6) and 0 to 50.0% by weight of units of the general formula (7), with the proviso that the sum of the units of the general formulae (6) and (7) is at least 1% by weight.

Organopolysiloxane particles which are built up at least to the extent of 80 mol % of units of the general formulae (2) and (5) have elastomeric properties. These particles are swellable in the above organic solvents, in particular in toluene, tetrahydrofuran, dioxane, petroleum ether and chlorinated hydrocarbons, such as $H_2CCl_2$ and $HCCl_3$. Metal complexes of, for example, compounds which are to be reacted can also be achieved even in the interior in these organopolysiloxane particles in the swollen state.

The invention furthermore relates to a process for the preparation of the crosslinked organopolysiloxane particles which carry chemically bonded metal compounds, in which, in a first step, by metering silanes of the general formula (12)

and, if appropriate, organosilicon compounds which are built up from units of the general formula (13)

into an agitated mixture of emulsifier and water, a colloidal suspension of organopolysiloxane particles is prepared, in a second step, silanes of the general formula (14)

and/or organosilicon compounds which are built up from units of the general formula (15)

are added to the colloidal suspension, with the proviso that the compounds which are built up from units of the general formula (15) contain at least one radical A and one radical ($R^2O$), and, in a third step, an organosilicon compound of the general formula (16)

is added to the colloidal suspension, with the proviso that the organosilicon compounds of the general formula (16) are water-soluble or hydrolyze in water to give a water-soluble compound, in which $R^2$ and $R^4$ have the meanings of R, $R^3$ has the meanings of A or R, X, if h=1, is —OR⁵, —ONR⁵₂ or —OOCR⁵ and if h=2, is —O— or —S—, $R^5$ has the meanings of R, a has the values 0, 1, 2 or 3, b and c, in each case independently of one another, have the values 0, 1, 2, 3 or 4, d has the values 0, 1 or 2, e, f and g, in each case independently of one another, have the values 0, 1, 2 or 3, h has the values 1 or 2 and R and A have the above meanings.

Interparticle condensation of the organopolysiloxane particles is prevented by a procedure in which the groups which are capable of condensation and remain after the first and second step are neutralized with organosilicon compounds containing exclusively monofunctional triorganosilyl groups.

Preferably, no by-products, such as hydrochloric acid or ammonia, which substantially increase the ionic strength of the aqueous colloidal system are formed in the hydrolysis or condensation reaction of the organosilicon compounds of the general formula (16).

Organosilicon compounds of the general formula (16) which are particularly preferably employed are trialkylalkoxysilanes, such as trimethylmethoxysilane and trimethylethoxysilane, and in these $R^2$ and $R^3$ are preferably methyl groups; and dimethylalkenalkoxysilanes, in which $R^2$ and $R^3$ are preferably allyl or vinyl radicals; $R^2$ and $R^3$ can likewise also be cyclic alkenes or alkadienes. Particularly preferred alkoxy radicals are the methoxy and ethoxy radical. Hexaalkyldisiloxanes, such as hexamethyldisiloxane, are furthermore preferred. Trimethylmethoxysilane and trimethylethoxysilane are particularly preferably employed in the third step.

When the third reaction step has ended, the organopolysiloxane particles can be isolated from the colloidal suspensions by known processes, for example by breaking the dispersion by means of addition of salt or by addition of polar solvents.

After isolation after the third step, organopolysiloxane particles which comprise more than 15% by weight in total of units of the general formulae (6) and (7) are preferably treated, in a fourth reaction step in an aprotic solvent, with an organosilicon compound of the general formulae (17)

$(R^6R^7{}_2Si)_iY$        (17), or (18)

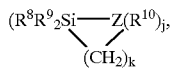
$(R^8R^9{}_2Si{-}Z(R^{10})_j$, with $(CH_2)_k$    (18)

in which $R^6$ and $R^8$ have the meanings of A or R, $R^7$, $R^9$ and $R^{10}$ have the meanings of R, Y, if i=1, is halogen atoms, $-OR^6$, $-NR^6{}_2$, $-ONR^6{}_2$ or $-OOCR^6$ and if i=2, is $-O-$, $=N(R^6)$ or $-S-$, Z, if j=1, is $-N-$ and if j=0, is $-O-$ or $-S-$, i has the values 1 or 2, j has the values 0 or 1, k has values from 1 to 30 and R and A have the above meanings.

Organosilicon compounds of the general formulae (17) and (18) which are particularly preferably employed in this fourth reaction step are alkylchlorosilanes, such as trimethylchlorosilane, dimethylchlorosilane or vinyldimethylchlorosilane, hexamethyldisilazane, 1,3-divinyl-1,1,3,3-tetramethyldisilazane or mixtures of disilazanes and/or chlorosilanes.

The amount of compounds of the general formulae (12) to (18) employed are chosen such that the desired organopolysiloxane particles are obtained. The amounts of compounds of the general formulae (12) and (13) employed are incorporated virtually quantitatively in the first reaction step and control the degree of crosslinking of the organopolysiloxane particles in aqueous suspension.

The metal compound density on the surface of the organopolysiloxane particles is preferably controlled by the amount of compounds of the general formulae (14) and (15) employed in the second reaction step. Preferably, 0.001 to 0.5, in particular 0.01 to 0.1, part by weight of compounds of the general formulae (14) and (15) is used per part by weight of compounds of the general formulae (12) and (13).

Compounds of the general formulae (16) to (18) employed in the third and, if appropriate, in the fourth reaction step are in each case employed in excess and are thus not incorporated completely into the organopolysiloxane particles. Preferably, 0.01 to 10, in particular 0.1 to 1, parts by weight of compounds of the general formulae (16), in the third reaction step, or of the sum of the compounds of the general formulae (16) to (18), in the third and fourth reaction step, are employed per part by weight of compounds of the general formulae (12) and (13).

If a fourth reaction step is carried out, the ratio of the amount of compounds of the general formulae (16) employed in the third reaction step to the amount of compounds of the general formulae (16) to (18) employed in the fourth reaction step is preferably 1:10 to 2:1, in particular 1:5 to 1:1.

The radical R in the compounds employed in the process is preferably unsubstituted $C_1$- to $C_6$-alkyl radicals and the phenyl radical where methyl, ethyl and propyl radicals are particulaly preferred.

The ligand units A in the general formulae (14) to (18) can already be bonded in a complex of the general formulae (10) or (11), or prepared after the second, third or fourth step by reaction of a ligand unit with a metal compound.

Examples of suitable metal compounds are $FeB_3$, $FeB_2$, $CoB_3$, $CoB_2$, $NiB_2$, $RuB_3$, $RuB_2$, $RhB3$, $RhB_2$, $RhB$, $Rh(diene)B$, $RhB(CO)$, $PdB_4$, $PdB_2$, $OsB_3$, $IrB_3$, $IrB$, $Ir(diene)B$, $IrB(CO)$, $PtB_4$ and $PtB_2$, in which B is a chlorine, bromine, iodine or hydrogen atom or acetylacetonate, acetate, 0.5 $SO_4$, $NO_3$ or CN and diene is cyclooctadiene or norbornadiene.

Complex compounds, such a $FeB_3L_3$, $FeB_2L_4$, $CoB_3L_2$, $CoB_3L_3$, $CoB_2L_3$, $COB_2L_4$, $NiB_2L_2$, $NiL_4$, $RuB_3L_3$, $RhB_3L_3$, $RhB_2L_3$, $RhBL_3$, $RhL^{4+}B^-$, $PdB_4L_2$, $PdB_2L_2$, $PdL_4$, $OsB_3L_3$, $IrB_3L_3$, $IrBL_3$, $PtB_4L_2$, $PtB_2L_2$ and $PtL_4$, in which and L have the above meanings, can also be employed as metal compounds.

Emulsifiers which are particularly suitable in the preparation process are:

alkyl sulfates, for example having a chain length of 8–18 C atoms, and aryl and alkyl ether sulfates having 8–18 C atoms in the hydrophobic radical and 1–40 ethylene oxide (EO) or propylene oxide (PO) units;

sulfonates, for example alkylsulfonates having 8–18 C atoms, alkylarylsulfonates having 8–18 C atoms and esters and half-esters of sulfosuccinic acid with monohydric alcohols or alkylphenols having 4–15 C atoms; these alcohols or alkylphenols can optionally also be ethoxylated with 1–40 EO units;

alkali metal and ammonium salt of carboxylic acids having 8–20 C atoms in the alkyl, aryl, alkaryl or aralkyl radical;

phosphoric acid partial esters and alkali metal and ammonium salts thereof, for example alkyl and alkaryl phosphates having 8–20 C atoms in the organic radical, and alkylether- or alkarylether-phosphates having 8–20 C atoms in the alkyl or alkary radical and 1–40 EO units;

alkylpolyglycol ethers having 2–40 EO units and alkyl radicals of 4–20 C atoms;

alkylarylpolyglycol ethers having 2–40 EO units and 8–20 C atoms in the alkyl and aryl radicals;

ethylene oxide/propylene oxide (EO/PO) block copolymers having 8–40 EO and PO units;

fatty acid polyglycol esters having 6–24 C atoms and 2–40 EO units;

alkyl polyglycosides, natural substances and derivatives thereof, such a lecithin, lanolin, saponins and cellulose; and cellulose alkyl ethers and carboxyalkylcelluloses, the alkyl groups of which in each case have up to 4 carbon atoms;

linear organo(poly)siloxanes which contain polar groups and have alkoxy groups having up to 24 C atoms and/or up to 40 EO and/or PO groups;

salts of primary, secondary and tertiary fatty amines having 8–24 C atoms with acetic acid, sulfuric acid, hydrochloric acid and phosphoric acids;

quaternary ammonium salts, such as halides, sulfates, phosphates, acetates or hydroxides, the alkyl groups of which independently of one another have 1–24 C atoms; the alkyl or alkaryl or a alkyl groups of the quaternary ammonium compounds an also optionally be partly ethoxylated (1–40 EO units);

alkylpyridinium, alkylimidazolinium and alkyloxazolinium salts, the alkyl chain of which has up to 18 C atoms, in the form of their halides, sulfates, phosphates or acetates.

Benzenesulfonic acids with aliphatic substituents and salts thereof and optionally partly ethoxylated quaternary ammonium halides and hydroxides are preferred. Dodecylbenzenesulfonic acid and benzyldimethyl-{2-[2-(p-1,1,3,3-tetramethylbutyl-phenoxy)ethoxy]ethyl}ammonium chloride (benzethonium chloride) are particularly preferred.

The amount of emulsifier to be employed is 0.5–50% by weight, preferably 1.0–30% by weight, in each case based on the total amount of organosilicon starting compounds employed in the first, second and third reaction step. The organosilicon starting compounds of the general formulae (12) and (13) are preferably added by metering in during the first reaction step. Preferably, all the starting components of the general formulae (12) and (13) are mixed in the desired ratio before the metering during the first reaction step; in order to obtain a homogeneous mixture, 0.1–30% by weight, based on the sum of the starting components of the general formulae (12) and (13), of alkanol of the formula $R^{11}OH$, in which $R^{11}$ is an alkyl radical having 1 to 5 carbon atoms, is optionally also added as a solubilizing agent, the alkanols methanol and ethanol being particularly preferred.

Aprotic organic solvents which are used in the fourth reaction step are peferably the ethers, hydrocarbons, ketones and organpolysiloxanes described above, in particular tetrahydrofuran, cyclohexane, methylcyclohexane or toluene. The reaction both in the first (emulsion polycondensation/polymerization) and in the second and third reaction step is preferably carried out at 5–95° C., in particular at 10–85° C., and particularly preferably at 10–40° C. The pH is in each case 1–12, preferably 1–4 or 7–11, depending on the acid/base stability of the radicals R, $R^1$, $R^2$, $R^3$, $R^4$ and $R^5$ of the starting compounds (12) to (16).

In the preparation of the colloidal suspensions during the first reaction step, it is advantageous for the stability of the emulsion to subsequently stir the mixture for a further 1 to 24 hours after the end of metering of the organosilicon starting compounds of the general formulae (12) and (13). The alkanol liberated during the hydrolysis can be removed by distillation, if appropriate under reduced pressure, although this is not preferred. The solids content of the colloidal suspension prepared after the first step should preferably be not more than 25% by weight, since otherwise a high increase in the viscosity makes further reaction more difficult. In the reaction of the colloidal suspension with the organosilicon compound of the general formula (14) and (15) in the second reaction step, it is likewise advantageous, in order to achieve a reaction which is as complete as possible, to subsequently stir the mixture for a further 1–48 hours after the end of the addition of compounds of the general formula (12) and (13).

The reaction with the organosilicon compounds of the general formulae (17) and (18) in the fourth reaction step is preferably carried out at 5–95° C., in particular at 10–85° C., and particularly preferably at 10–40° C. To achieve a reaction which is as complete as possible, it is again advantageous to subsequently stir the mixture for a further 1–24 hours after the end of the addition of the compound of the general formulae (12) and (13).

If silicon compounds which contain several sites which are capable of hydrolysis or condensation are employed in the second, third or fourth step, additional shells can be formed on the surface of the organopolysiloxane particles.

In the preparation of organopolysiloxane particles of at least 80 mol % of silanes of the general formulae (12), in which a has the value 2, and (14), in which d has the value 1, the first and second step can be combined to one step. A colloidal suspension of organopolysiloxane particles is prepared in this step by metering compounds of the general formulae (12) to (15) together into an agitated mixture of emulsifier and water. Since these organopolysiloxane particles are swellable elastomers, the metal compounds inside the particles are readily accessible, for example for further catalytic reactions.

If no metal compound is present in the compounds of the general formula (14) to (18) in the preparation of the organopolysiloxane particles, the particles are reacted in a further step with a metal compound to give organopolysiloxane particles which carry chemically bonded metal compounds. The metal compound employed can be a metal salt or a metal complex compound. The ligands on the organopolysiloxane particles, such as amino, mercapto and alkyl halide groups, can also be further modified chemically before the reaction with metal compounds.

If reactive groups, such as alkenyl or Si—H groups, are present on the particle in the preparation of organopolysiloxane particles which are soluble in organic solvents, silicon compounds containing ligands can be bonded to reactive groups in a further step. For example, silicon compounds containing Si—H groups and ligands can be bonded to the alkenyl groups with the aid of a hydrosilylation catalyst. Silicon compounds containing alkenyl groups and ligands, for example, can be bonded to the Si—H groups with the aid of a hydrosilylation catalyst.

If silanol groups are still present on the surface after the third step in the preparation of the organopolysiloxane particles, complexes can be formed in a further step with metal halide compounds, hydrogen halide being split off.

Static and dynamic light scattering is particularly suitable for structural characterization of the organopolysiloxane particles which carry chemically bonded metal compounds. Static and dynamic light scattering are established methods, which are known to the expert, in macromclecular chemistry and colloidal chemistry for the characterization of disperse particles. In static light scattering, the scattered intensity at various angles is averaged over a sufficiently long interval of time to provide information on the static properties of the macromolecules, such as the weight-average molecular weight $M_w$, the z-average of the square of the radius of gyration $<R_g^2>_z$, and the second virial coefficient $A_2$, which describes the intra- and intermolecular thermodynamic interactions of the disperse particles with the solvent. In contrast to static light scattering, fluctuation of the scattered light intensity as a function of time is observed in the case of dynamic light scattering. This leads to information on the dynamic properties of the molecules investigated. The z-average of the diffusion coefficient $D_z$ and thus, via the Stokes-Einstein law, the hydrodynamic radius $R_h$ and the coefficient $k_d$, which describes the dependence of the diffusion coefficient on the concentration, are measured. From the angular dependence of the scattered light the particle shape can be determined and any structuring present in solution can be clarified. Simultaneous static and dynamic light scattering measurement allows the abovementioned conclusions on the system investigated to be made with a single experiment, and therefore information on, for example, particle size, dispersity and shape and on molecular weight and density to be obtained. This is described, for example, in M. Schmidt, Simultaneous Static and Dynamic Light Scattering: Applications to Polyper Structure Analysis, in: Dynamic Light Scattering: The Method and some Applications; Brown, W. (Editor); Oxford University Press, Oxford, UK, 372–406 (1993).

The quotient of the radius of gyration and hydrodynamic radius, the so-called ρ ratio, provides structural information on the particle shape, such as hard sphere, hollow sphere, coil, rod or star polymer. For the particle shape "hard spheres", the theoretical ρ ratio is 0.775; the values measured for the preferred organopolysiloxane particles are from 0.775 to not more than ρ=1.0. The preferred organopolysiloxane particles are therefore spherical.

The size range of he organopolysiloxane particles represents the boundary between large molecules, oligomers and dendrimers on the one hand and small solid bodies on the other hand, and thus corresponds to a joining point between solid body and molecule. On the one hand, collective solid body properties have not yet developed; on the other hand, molecular behavior can no longer be observed or can be observed only in part. Examples of particulate structures of this order of size of virtually fixed conformation are microgels. According to Antonietti (Angew. Chemie 100 (1988) 1813–1817), microgels which are obtained from aqueous colloidal systems and have particle diameters in the mescscopic size range and molecular weights from $10^6$ to $10^{11}$ g/mol are called "Type B" microgels.

The organopolysiloxane particles which carry chemically bonded metal compounds can be employed in many reactions and reaction systems as catalysts, in particular homogeneous catalysts, in which, however, the catalytically active complex is immobilized or heterogenized on the soluble, mesoscopic support particle. Examples of catalyst uses are hydroformylation, hydrogenation of multiple bonds, hydrosilylation, radiation-induced catalytic reactions and olefin polymerization.

In the Examples which follow, unless stated otherwise in each case, a) all the amounts data are based on the weight;
b) all pressures are 0.10 MPa (absolute);
c) all temperatures are 20° C.

EXAMPLES

The particle size is measured by means of light scattering:

Static and dynamic light scattering are measured with a unit which comprises, inter alia, a Stabilite® TM 2060-lls Kr laser from Spectra-Physics, an Sp-86 goniometer from ALV and an ALV-3000 digital structurator/correlator. The krypton ion laser operates with a wavelength of 647.1 nm.

Sample preparation: The samples of the organopolysiloxane particles in an appropriate solvent are filtered three times through Millex® TM-FGS filter (0.2 μm pore size) from Millipore. The concentration range is in each case 0.5–2 g/l. The measurement temperature in the light scattering experiments is 20° C. The dynamic light scattering measurements are carried out as a function of the angle from 50° to 130° in 20° steps, and the correcation functions are evaluated with the Simplex algorithm. In the static light scattering experiment, the angular dependence of the scattered light is measured from 30° to 140° in 5° steps.

Synthesis of Base Dispersion I 100 g of methyltrimethoxysilane are metered into an initial mixture of 500 g of water and 2 g of dodecylbenzenesulfonic acid at room temperature in the course of 90 minutes. The reaction solution is then stirred for 3 hours.

Synthesis of Base Dispersion II 100 g of a mixture of 95 g of dimethyldimethoxysilane and 5 g of methyltrimethoxysilane are metered into an initial mixture of 500 g of water and 5 g of dodecylbenzenesulfonic acid at 80° C. in the course of 90 minutes. The reaction solution is then stirred at 80° C. for 3 hours.

Example 1

Amino-functionalized Organopolysiloxane Particles

In each case 5 g of a trimethoxyalkylamine listed in Table 1 are metered into 100 g of base dispersion I at room temperature, while stirring. The dispersions are subsequently stirred at room temperature for three hours.

3 g of trimethylmethoxysilane are added to in each case 52.5 g of the resulting amino-functionalized base dispersions at room temperature. After being stirred for a further 15 hours, the dispersions are broken with 100 ml of methanol and filtered. After the solid has been washed three times with 50 ml of methanol each time, it is taken up in toluene, 4 g of hexamethyldisilazane are added and the mixture is stirred at room temperature for 10 hours. The amino-functionalized microgel particles are precipitated with 200 ml of methanol, filtered off, rinsed with two portions of 50 ml of methanol and dried under a high vacuum. White powders are obtained.

TABLE 1

| Trimethoxyalkylamine | Abbreviation | Yield [g] | Particle size [nm] |
|---|---|---|---|
| $N[(CH_2)_3Si(CH_3O)_3]_3$ | Amine I | 5.0 | 11 |
| $HN[(CH_2)_3Si(CH_3O)_3]_2$ | Amine II | 4.8 | 12 |
| $CH_3N[(CH_2)_3Si(CH_3O)_3]_2$ | Amine III | 4.9 | 11 |
| $(CH_3O)_3Si(CH_2)_3NH(CH_2)_2NH_2$ | Diamine | 5.1 | 13 |

Example 2

Amino-functionalized Organopolysiloxane Particles 6 g of dimethyl-3-(methylamino)propylmethoxysilane are added to 100 g of base dispersion I while stirring and the mixture is stirred at room temperature for 15 hours. The dispersion is broken with 250 ml of methanol and filtered and the residue on the filter is rinsed three times with 50 ml of methanol each time. It is taken up in toluene and reacted with 6 g of 1,1-dimethyl-1-sila-2-methyl-2-azacyclopentane, and the mixture is stirred at room temperature for 10 hours. The product is precipitated in 200 ml of methanol, filtered off, rinsed with two portions of 50 ml of methanol and dried under a high vacuum. 8.2 g of a white powder are obtained. The particle size is 14 nm.

Example 3

Phosphino-functionalized Organopolysiloxane Particles (All work is carried out under the inert gas argon, and the solvents used are degassed and then saturated with argon)

5 g of the phosphinotrimethoxysilane compounds listed in Table 2 are metered into in each case 100 g of degassed and argon-saturated base dispersion I at room temperature, while stirring. The dispersions are subsequently stirred at room temperature for three hours.

6 g of trimethylmethoxysilane are added to the phosphino-functionalized dispersions at room temperature. After the dispersions have been stirred for a further 15 hours, they are broken with 250 ml of methanol and filtered. After the solid has been washed three times with 50 ml of methanol each time, it is taken up in toluene, 8 g of hexamethyldisilazane are added and the mixture is stirred at room temperature for a further 10 hours. The products are precipitated in 300 ml of methanol, filtered off, washed twice with 70 ml of methanol each time and dried under a high vacuum. All the products are white powder.

TABLE 2

| Phosphinotrimethoxysilane compounds | Abbreviations | | Yield [g] | Particle size [nm] |
|---|---|---|---|---|
| $(CH_3)_2P(CH_2)_3Si(OCH_3)_3$ | Phosphine I | | 9 | 11.6 |
| $C_6H_5P[(CH_2)_3Si(OCH_3)_3]_2$ | Phosphine II | | 8.5 | 12.1 |
| $(C_6H_5)(CH_3)P(CH_2)_2(CH_3)P(CH_2)_3Si(OCH_3)_3$ | Diphosphine | | 10.8 | 13.0 |

Example 4

Cycloodieno-functionalized Organopolysiloxane Particles

In each case 4 g of trimethylmethoxysilane are added to in each case 100 g of base dispersion I at room temperature, while stirring. The dispersions are stirred for 15 hours and then broken with 200 ml of methanol and filtered. After the solid has been washed three times with 50 ml of methanol each time, it is taken up in toluene, 6 g of a dimethyl(3-cyclodienyl)propylchlorosilane listed in Table 3 are added and the mixture is stirred at room temperature for 16 hours. 2 g of trimethylchlorosilane are then added to the solution and the mixture is stirred at room temperature for a further 10 hours. The product is precipitated with methanol, filtered off, rinsed with two portions of 75 ml of methanol and dried under a high vacuum.

TABLE 3

| Dimethyl(3-cyclodienyl)-propylchlorosilane | Abbreviation | | Yield [g] | Particle size [nm] |
|---|---|---|---|---|
| $(C_5H_4)(CH_2)_3Si(CH_3)_2Cl$ | cyclopentyl | cp | 8.4 | 14.6 |
| $(C_{13}H_9)(CH_2)_3Si(CH_3)_2Cl$ | fluorenyl | flu | 7.5 | 16.8 |
| $(C_9H_7)(CH_2)_3Si(CH_3)_2Cl$ | indenyl | ind | 7.9 | 16.1 |

Example 5

Pyridino-functionalized Organopolysiloxanes 4 g of trimethylmethoxysilane are added to 100 g of base dispersion I at room temperature, while stirring, and the mixture is stirred for 15 hours. The dispersion is broken with 200 ml of methanol and filtered and the residue on the filter is rinsed with three portions of 60 ml of methanol. It is taken up in toluene, 6 g of 2-ethyl-pyridyl-dimethylchlorosilane are added and the mixture is stirred at room temperature for 16 hours. Thereafter, 2 g of trimethylchlorosilane are added and the mixture is stirred at room temperature for a further 10 hours. The product is precipitated with methanol, rinsed with two portions of 75 ml of methanol and dried under a high vacuum. 7.6 g of a slightly yellowish powder are obtained. The particle size is 14.5 nm.

Example 6

Titanium Dichloride-functionalized Organopolysiloxane Particles 4 g of trimethylmethoxysilane are added to 100 g of base dispersion I at room temperature, while stirring, and the mixture is stirred for 15 hours. The dispersion is broken with 200 ml of methanol and filtered and the residue on the filter is rinsed with methanol. It is dissolved in 500 ml of toluene. The solution is then concentrated to 50 ml, 400 ml of toluene are again added and the mixture is concentrated again down to 50 ml. 4 g of titanium tetrachloride are added to the solution which remains and the mixture is stirred at room temperature for 16 hours. The solvent is distilled off. The residue is dried under a high vacuum. 9.5 g of product are obtained.

Example 7

(All work is carried out under the inert gas argon, and the solvents used are degassed and then saturated with argon)

4 g of trimethylmethoxysilane are metered into 100 g of degassed and argon-saturated base dispersion I at room temperature, while stirring, and the mixture is stirred for 15 hours. The dispersion is broken with 200 ml of methanol and filtered and the residue on the filter is rinsed with methanol. It is treated with the same amounts of solvent as in Example 6. Metal-phosphine complexes of the general formula $Cl_2M[(C_6H_5)(CH_3)P(CH_2)_3Si(CH_3)_2Cl$, in which M=Pt or Pd, are added to the resulting toluene solution and the mixture is stirred at room temperature for 10 hours. 2 g of trimethylchlorosilane are then added, the mixture is stirred at room temperature for a further 10 hours and the product is precipitated with 200 ml of methanol, filtered off, rinsed with methanol and dried under a high vacuum.

TABLE 4

| Mesoscopic metal-amine complexes | | | |
|---|---|---|---|
| Metal M | Abbreviation | Yield [g] | Particle size [nm] |
| Pt | Pt comple I | 8.3 | 15.2 |
| Pd | Pd complex I | 7.4 | 12.6 |

Example 8

5g of a metal-amine complex of the general formula $Cl_2M[H_2N(CH_2)_2NH(CH_2)_3Si(OCH_3)_3]$, in whigh M=Pt or Pd, are metered into 100 g of base dispersion I at room temperature, while stirring. The dispersions are subsequently stirred at room temperature for three hours.

4 g of trimethylmethoxysilane are then added to the dispersion at room temperature, while stirring. After the dispersions have been stirred for a further 15 hours, they are broken with 200 ml of methanol and filtered and the solid is rinsed with three portions of 50 ml of methanol. It is taken up in toluene, 8 g of hexamethyldisilazane are added and the mixture is stirred at room temperature for 10 hours. The mesoscopic complex compound is precipitated with 200 ml of methanol, filtered off, rinsed with two portions of 50 ml of methanol and dried under a high vacuum.

TABLE 5

| Metal M | Abbreviation | Yield [g] | Particle size [nm] |
|---|---|---|---|
| Pt | Pt complex II | 7.8 | 12.0 |
| Pd | Pd complex II | 8.2 | 16.6 |

Example 9

Amino-functionalized Elastomer Particles/amine IV 5 g of $H_2N(CH_2)_3Si(CH_3)_2(OCH_3)$ are added to 100 g of base dispersion II at room temperature, while stirring, and stirring is continued for 15 hours. The dispersion is broken in 200 ml of methanol and filtered. The residue on the filter is taken up in 70 ml of toluene, precipitated again with 250 ml of methanol, filtered off and dried under a high vacuum. 10.2 g of product are obtained. The particle radius in toluene is 40 nm.

Example 10

Phosphino-functionalized Elastomeric Organopolysiloxane (All work is carried out under the inert gas argon, and the solvents used are degassed and then saturated with argon)

6 g of $(C_6H_5)(CH_3)P(CH_2)_2Si(CH_3)_2(OCH_3)$ are added to 100 g of degassed and argon-saturated base dispersion II at room temperature, while stirring, and stirring is continued for 15 hours. The dispersion is broken with 200 ml of methanol and filtered. The residue on the filter is dissolved in 70 ml of toluene and precipitated again with 250 ml of methanol, filtered off and dried under a high vacuum. 8.9 g of product having a particle radius in toluene of 43 nm are obtained.

Example 11

Phosphino-functionalized Elastomeric Organopolysiloxane (All work is carried out under the inert gas argon, and the solvents used are degassed and then saturated with argon)

A mixture of 23.75 g of dimethyldimethoxysilane, 0.5 g of methyltrimethoxysilane and 0.6 g of $(C_6H_5)(CH_3)P(CH_2)_2Si(OCH_3)_3$ is metered into an initial mixture of 125 g of water and 1.25 g of dodecylbenzenesulfonic acid at 80° C. in the course of 90 minutes. The reaction solution is then stirred at 80° C. for three hours.

After the dispersion has been cooled to room temperature, 6 g of trimethylmethoxysilane are added and the mixture is stirred at room temperature for 15 hours. The dispersion is then broken with 300 ml of methanol and filtered and the residue on the filter is taken up in 100 ml of toluene. The product is precipitated from the toluene solution with 300 ml of methanol. 16.5 g of product which has a particle radius of 65 nm in toluene are obtained.

Example 12

(All work is carried out under the inert gas argon, and the solvents used are degassed and then saturated with argon)

A mixture of 23.75 g of dimethyldimethoxysilane, 0.5 g of methyltrimethoxysilane and 0.75 g of a metal-phosphine complex of the general formula $Cl_2M[(C_6H_5)(CH_3)P(CH_2)_2Si(OCH_3)_3]_2$, the metal M of which is listed in Table 6, is metered into an initial mixture of 125 g of water and 1.25 g of dodecylbenzenesulfonic acid at room temperature in the course of 120 minutes. The dispersion is stirred at room temperature for a further three hours.

6 g of trimethylmethoxysilane are then added to the dispersion at room temperature, while stirring, and the mixture is subsequently stirred for 15 hours. The dispersion is broken in 300 ml of methanol and filtered and the residue on the filter is taken up in 100 ml of toluene and precipitated again with 200 ml of methanol. The residue on the filter is rinsed with methanol and dried under a high vacuum.

TABLE 6

Metal-phosphine complexes with mesoscopic elastomeric ligands

| Metal M | Abbreviation | Yield [g] | Particle size [nm] |
|---|---|---|---|
| Pt | Pt complex III | 10.6 | 60 |
| Pd | Pd complex III | 11.3 | 65 |
| Ru | Ru complex I | 9.9 | 70 |
| Rh | Rh complex I | 10.8 | 58 |

Example 13

Coordination Compounds with Mesoscopic Amine Ligands (All work is carried out under the inert gas argon, and the solvents used are degassed and then saturated with argon)

A metal compound in a suitable solvent mentioned in Table 7 is added to a 1% strength solution of a mesoscopic amino-functionalized complex ligand, mentioned in Table 7, in 10 ml of toluene at room temperature, while stirring. The solution is then heated at 60° C. for 4 hours. The product is precipitated, filtered off and dried under a high vacuum. The yields are listed in Table 7. cod means cyclooctadiene.

TABLE 7

Synthesized complexes with amino-functional mesoscopic ligands

| Metal compound employed [g] | | Solvent for the metal compound | Complexing ligand | Yield [g] | Abbreviation |
|---|---|---|---|---|---|
| [RhCl(cod)]$_2$ | 0.25 | Ethanol/2 ml | Amine I | 0.60 | Rh complex II |
| [RhCl(cod)]$_2$ | 0.1 | " | Amine IV | 0.50 | Rh complex III |
| PdCl$_2$ | 0.2 | Methanol/1 ml | Amine I | 0.55 | Pd complex IV |
| PdCl$_2$ | 0.1 | " | Amine IV | 0.45 | Pd complex V |
| IrCl$_3$3H$_2$O | 0.22 | Ethanol/2 ml | Amine I | 0.5 | Ir complex I |
| RuCl$_3$3H$_2$O | 0.2 | Ethanol/2 ml | Amine I | 0.45 | Ru complex II |
| RuCl$_3$3H$_2$O | 0.1 | " | Amine IV | 0.4 | Ru complex III |
| H$_2$PtCl$_6$ | 0.2 | Ethanol/2 ml | Amine I | 0.6 | Pt complex IV |
| H$_2$PtCl$_6$ | 0.1 | " | Amine IV | 0.5 | Pt complex V |
| H$_2$PtCl$_6$ | 0.1 | " | Diamine | 0.45 | Pt complex VI |
| FeCl$_3$3H$_2$O | 0.2 | Ethanol/3 ml | Amine I | 0.4 | Fe complex I |
| Co(O$_2$CCH$_3$)$_2$4H$_2$O | 0.2 | Ethanol/2 ml | Amine I | 0.5 g | Co complex I |

TABLE 7-continued

Synthesized complexes with amino-functional mesoscopic ligands

| Metal compound employed [g] | | Solvent for the metal compound | Complexing ligand | Yield [g] | Abbreviation |
|---|---|---|---|---|---|
| NiSO$_4$6H$_2$O | 0.2 | Ethanol/2 ml | Diamine | 0.6 | Ni complex I |
| OsCl$_3$ | 0.2 | Ethanol/2 ml | Amine I | 0.5 | Os complex I |
| CuCl | 0.1 | Suspension in methanol/2 ml | Amine II | 0.45 | Cu complex I |
| WCl$_6$ | 0.2 | Ethanol/2 ml | Amine I | 0.5 | W complex I |
| MoCl$_5$ | 0.2 | Chloroform/2 ml | Amine III | 0.4 | Mo complex I |
| MnSO$_4$ | 0.2 | Methanol/2 ml | Amine III | 0.55 | Mn complex I |
| ReCl$_5$ | 0.2 | Ethanol/2 ml | Amine I | 0.5 | Re complex I |
| AuCl$_3$ | 0.2 | Ethanol/2 ml | Amine I | 0.4 | Au complex I |
| AgNO$_2$ | 0.2 | Methanol/2 ml | Amine I | 0.4 | Ag complex I |

Example 14

Mixed Coordination Compounds with Mesoscopic Amino Ligands

(All work is carried out under the inert gas argon, and the solvents used are degassed and then saturated with argon)

A mixture of 0.1 g of H$_2$PtCl$_6$ and 0.1 g of RuCl$_3$ in 3 ml of methanol is added to an initial mixture of 20 ml of toluene and 0.5 g of the mesoscopic amino ligands (amine I) from Example 1 at room temperature, while stirring. The mixture is then stirred for a further 4 hours. The product is precipitated with methanol, filtered off and dried under a high vacuum. 0.55 g of product is obtained.

Example 15

Mesoscopic Coordination Compounds with Phosphino Ligands

(All work is carried out under the inert gas argon, and the solvents used are degassed and then saturated with argon)

A metal compound listed in Table 8 in a suitable solvent is added to an initial mixture of 20 ml of toluene and 0.5 g of a mesoscopic complexing ligand from Example 3 at room temperature, while stirring. The reaction solution is stirred for a further 4 hours. The product is precipitated with methanol, filtered off and dried under a high vacuum.

TABLE 8

Synthesized complexes with phosphino-functionalized mesoscopic ligands

| Metal compound employed | [g] | Solvent for the metal compound | Complexing ligand | Yield [g] | Abbreviations |
|---|---|---|---|---|---|
| RhCl$_3$(CH$_3$CN)$_3$ | [0.2] | Ethanol/2 ml | Phosphine II | 0.55 | Rh complex III |
| " | [0.1] | " | Phosphine III | 0.4 | Rh complex IV |
| PdCl$_2$ | [0.2] | Ethanol/2 ml | Phosphine I | 0.5 | Pd complex V |
| " | [0.1] | Methanol/1 ml | Phosphine III | 0.55 | Pd complex VI |
| IrCl$_3$3H$_2$O | [0.2] | Ethanol/2 ml | Phosphine I | 0.45 | Ir complex II |
| RuCl$_3$3H$_2$O | [0.2] | Ethanol/2 ml | Phosphine I | 0.5 | Ru complex IV |
| H$_2$PtCl$_6$ | [0.2] | Ethanol/2 ml | Phosphine II | 0.45 | Pt complex VII |
| " | " | " | Diphosphine | 0.5 | Pt complex VIII |
| FeCl$_3$3H$_2$O | [0.2] | Methanol/3 ml | Phosphine II | 0.4 | Fe complex II |
| Co(O$_2$CCH$_3$)$_2$4H$_2$O | [0.2] | Ethanol/2 ml | Phosphine I | 0.45 | Co complex II |

Example 16

Coordination Compounds with Mesoscopic Cyclodiene Ligands

(All work is carried out under the inert gas argon, and the solvents used are degassed and then saturated with argon)

1 g of the cyclodiene-functionalized organopolysiloxane particles prepared in Example 4 is dissolved in 50 ml of diethyl ether at room temperature, and 2.0 ml of butyllithium (1.6 M in hexane) are added. After the mixture has been stirred for 10 minutes, 0.4 g of CP$_2$MCl$_2$, in which M=Zr; Hf or Ti, is added and the mixture is stirred for a further 30 minutes. The resulting suspension is filtered over sodium sulfate and rinsed with two portions of 30 ml of ether. The metallocene complex compound is detached from the sodium sulfate with methylene chloride and the solvent is then stripped off again under a high vacuum.

TABLE 9

Metallocene complex compounds

| Central atom M | Mesoscopic ligand | Yield [g] | Abbreviation |
|---|---|---|---|
| Ti | Ind | 1.1 | Ti complex I |
|  | Flue | 1.0 | Ti complex II |
| Zr | Ind | 1.2 | Zr complex I |
|  | Flu | 1.1 | Zr complex II |
| Hf | Flu | 1.0 | Hf complex I |

Example 17

Coordination Compounds for Mesoscopic Heterocyclic Ligands

1 g of the pyridino-functionalized organopolysiloxane particles prepared in Example 5 are dissolved in toluene, and metal compounds listed in Table 10, which are dissolved or suspended in suitable solvents, are added. The reaction mixture is stirred at 70° C. for 4 hours. The resulting complex compounds are precipitated with methanol, filtered off and dried under a high vacuum.

TABLE 10

Synthesized compounds complex with mesoscopic pyridino ligands

| Metal compound | [g] | Solvent for the metal compound | Yield [g] | Abbreviation |
|---|---|---|---|---|
| $H_2PtCl_6$ | [0.2] | Methanol/2 ml | 1.1 | Pt complex IX |
| CuCl | | Suspended in methanol/3 ml | 1.0 | Cu complex II |

Example 18

Hydroformylation 0.4 g of Rh complex III from Example 15 is dissolved in 500 ml of 1-octene and the solution is introduced into an autoclave. The reaction is carried out under a total pressure of 200 bar and at a temperature of 100° C. and an $H_2$:CO ratio of 1:1.

Analysis by gas chromatography (GC) shows a 98% conversion of the octene into the corresponding aldehyde.

Example 19

Hydrogenation of Multiple Bonds 0.4 g of Pd complex V is dissolved in 100 ml of 1-octene and the solution is introduced into a 1 l autoclave. The reaction mixture is heated to 60° C. under a constant $H_2$ pressure of 5 bar and is stirred for 5 hours.

GC analysis shows that 95% of the 1-octene is hydrogenated to octane.

Example 20

Hydrosilylation 0.5 g of Pt complex II is dissolved in 22.15 g of 1-octene and 26.73 g of $HSiCl_3$. The reaction solution is introduced into a glass autoclave and heated at 100° C. for 24 hours, while stirring.

GC analysis of the product shows that 95% of the 1-octene employed has reacted to give octyltrichlorosilane.

Example 21

Olefin Polymerization
(All work is carried out under the inert gas argon, and the solvents used are degassed and then saturated with argon)
Activation of the Catalyst Precursor 50 mg of the particular mesoscopic metallocenedichloride complexes (Ti complex II, Zr complex I) from Example 16 are dissolved in 10 ml of toluene, and 2 ml of methylaluminum oxide, 30% strength by weight in toluene, $M_w$=1100 g/mol, are added. Olefin polymerization 500 ml of pentane are initially introduced into a 1 l autoclave at 10° C., 10 ml of the catalyst solution in toluene are added and an ethylene pressure of 10 bar is applied. The reaction mixture is kept at 60° C. for 1 hour, while stirring. The resulting polymer is filtered off and washed with dilute sodium hydroxide solution, water and acetone and solvent residues are removed in a drying cabinet.

TABLE 11

Yields of the olefin polymerization with mesoscopic metallocene catalysts

| Mesoscopic metallocene—dichloride complex | Yield of polyethylene [g] |
|---|---|
| Ti complex II | 30.5 |
| Zr complex I | 35.5 |

Example 22

Mesoscopic Catalyst Systems Activated Catalytically by Radiation Induction 0.4 g of platinum complex VI are suspended in 5 ml of methanol, 5 ml of a 0.1% strength solution of 1-phenyl-3-cyclohexyltriazene oxide potassium salt in methanol are added and the mixture is stirred at room temperature for two hours. The solid is filtered off and several extractions with toluene are carried out. The toluene solution is concentrated on a rotary evaporator and the resulting product is dried at room temperature under a high vacuum. 0.3 g of platinum complex X is obtained.

0.05 g of platinum complex X is dissolved in 5.4 g of 1-octene, and 8.2 g of triethoxysilane are added at room temperature, while stirring. The hydrosilylation reaction is initiated by UV irradiation (15 seconds with a wavelength of 350 nm). The reaction solution is subsequently stirred for a further 30 minutes.

GC analysis of the product shows that 96.5% of the 1-octene employed has reacted to give octyltriethoxysilane.

We claim:

1. Crosslinked organopolysiloxane particles which comprise a single molecule, have chemically bonded metal compounds, have an average diameter of 5 to 200 nm as determined by static and dynamic light scattering, and are soluble to the extent of at least 1% by weight in at least one of the solvents selected from the group consisting of methylene chloride, pentane, acetone, ethanol and water, at least 80% of the particles having a diameter which deviates not more than 30% from the average diameter.

2. Organopolysiloxane particles as claimed in claim 1, in which the average molecular weights are $10^5$ to $10^{10}$ g/mol.

3. Organopolysiloxane particles as claimed in claim 1, in which the metal compounds to which the organopolysiloxane particles are bonded chemically are selected from the metals of subgroup I, IV, VI, VII and VIII.

4. Organopolysiloxane particles as claimed in claim 2, in which the metal compounds to which the organopolysiloxane particles are bonded chemically are selected from the metals of subgroup I, IV, VI, VII and VIII.

5. Organopolysiloxane particles as claimed in claim 1, which have, on the surface, units which are selected from units of the general formulae

$[AR_2SiO_{1/2}]$ (1),

$[ARSiO_{2/2}]$ (2) and

$[ASiO_{3/2}]$ (3), and the remaining units of the organopolysiloxane particles comprise 0.5 to 80.0% by weight of units of the general formula

$[R_3SiO_{1/2}]$ (4), 0 to 99.0% by weight of units of the general formula $$[R_2SiO_{2/2}] \quad (5),$$

0 to 99.5% by weight of units of the general formula $$[RSiO_{3/2}] \quad (6) \text{ and}$$

0 to 80.0% by weight of units of the general formula $$[SiO_{4/2}] \quad (7),$$

in which

A is a ligand unit of the general formula $$spL' \quad (8) \text{ or}$$

$$spsp'L'' \quad (9)$$

at least one unit of the general formulae (8) or (9) per organopolysiloxane particle being bonded in a complex of the general formulae $$spL''_iML_k \quad (10) \text{ or}$$

$$spsp'L''_iML_k \quad (11)$$

and in which

M is a metal of subgroup I, IV, VI, VII or VIII of the Periodic Table of the Elements, L is a complexing ligand in the coordination sphere of the metal M, L' is a complexing ligand in the coordination sphere of the metal M bonded via a spacer sp to the surface of an organopolysiloxane particle, L'' is a complexing ligand in the coordination sphere of the metal M bonded via two spacers sp and sp' to the surface of an organopolysiloxane particle, sp and sp' are identical or different bivalent SiC-bonded, optionally substituted $C_1$- to $C_8$-hydrocarbon radicals, which can be interrupted by divalent radicals, bonded to carbon atoms on both sides, selected from the group consisting of —O—, —COO—, —OOC—, —CONR$^2$—, —NR$^2$CO—, —CO— and —[SiR$_2$]$_1$—, R is identical or different monovalent SiC-bonded, optionally halogen-substituted $C_1$- to $C_{18}$-alkyl radicals, i has values from 1 to not more than the coordination number of the metal M, k has values from 0 to not more than the coordination number of the metal M minus i and l has values from 1 to 100.

6. Organopolysiloxane particles as claimed in claim 2, which have, on the surface, units which are selected from units of the general formulae $$[AR_2SiO_{1/2}] \quad (1),$$

$$[ARSiO_{2/2}] \quad (2) \text{ and}$$

$$[ASiO_{3/2}] \quad (3),$$

and the remaining units of the organopolysiloxane particles comprise 0.5 to 80.0% by weight of units of the general formula $$[R_3SiO_{1/2}] \quad (4),$$

0 to 99.0% by weight of units of the general formula $$[R_2SiO_{2/2}] \quad (5),$$

0 to 99.5% by weight of units of the general formula $$[RSiO_{3/2}] \quad (6) \text{ and}$$

0 to 80.0% by weight of units of the general formula $$[SiO_{4/2}] \quad (7),$$

in which

A is a ligand unit of the general formula $$spL' \quad (8) \text{ or}$$

$$spsp'L'' \quad (9)$$

at least one unit of the general formulae (8) or (9) per organopolysiloxane particle being bonded in a complex of the general formulae $$spL''_iML_k \quad (10) \text{ or}$$

$$spsp'L''_iML_k \quad (11)$$

and in which

M is a metal of subgroup I, IV, VI, VII or VIII of the Periodic Table of the Elements, L is a complexing ligand in the coordination sphere of the metal M, L' is a complexing ligand in the coordination sphere of the metal M bonded via a spacer sp to the surface of an organopolysiloxane particle, L'' is a complexing ligand in the coordination sphere of the metal M bonded via two spacers sp and sp' to the surface of an organopolysiloxane particle, sp and sp' are identical or different bivalent SiC-bonded, optionally substituted $C_1$- to $C_8$-hydrocarbon radicals, which can be interrupted by divalent radicals, bonded to carbon atoms on both sides, selected from the group consisting of —O—, —COO—, —OOC—, —CONR$^2$—, —NR$^2$CO—, —CO— and —[SiR$_2$]$_1$—, R is identical or different monovalent SiC-bonded, optionally halogen-substituted $C_1$- to $C_8$-alkyl radicals, i has values from 1 to not more than the coordination number of the metal M, k has values from 0 to not more than the coordination number of the metal M minus i and l has values from 1 to 100.

7. Organopolysiloxane particles as claimed in claim 3, which have, on the surface, units which are selected from units of the general formulae $$[AR_2SiO_{1/2}] \quad (1),$$

$$[ARSiO_{2/2}] \quad (2) \text{ and}$$

$$[ASiO_{3/2}] \quad (3),$$

and the remaining units of the organopolysiloxane particles comprise 0.5 to 80.0% by weight of units of the general formula $$[R_3SiO_{1/2}] \quad (4),$$

0 to 99.0% by weight of units of the general formula $$[R_2SiO_{2/2}] \quad (5),$$

0 to 99.5% by weight of units of the general formula $$[RSiO_{3/2}] \quad (6)$$

and 0 to 80.0% by weight of units of the general formula $$[SiO_{4/2}] \quad (7),$$

in which
A is a ligand unit of the general formula $$spL' \quad (8)$$

or $$spsp'L'' \quad (9)$$

at least one unit of the general formulae (8) or (9) per organopolysiloxane particle being bonded in a complex of the general formulae $$spL''_iML_k \quad (10)$$

or $$spsp'L''_iML_k \quad (11)$$

and in which
M is a metal of subgroup I, IV, VI, VII or VIII of the Periodic Table of the Elements,
L is a complexing ligand in the coordination sphere of the metal M,
L' is a complexing ligand in the coordination sphere of the metal M bonded via a spacer sp to the surface of an organopolysiloxane particle,
L'' is a complexing ligand in the coordination sphere of the metal M bonded via two spacers sp and sp' to the surface of an organopolysiloxane particle, sp and sp' are identical or different bivalent SiC-bonded, optionally substituted $C_1$- to $C_{18}$-hydrocarbon radicals, which can be interrupted by divalent radicals, bonded to carbon atoms on both sides, selected from the group consisting of —O—, —COO—, —OOC—, —CONR²—, —NR²CO—, —CO— and —[SiR₂]₁—,
R is identical or different monovalent SiC-bonded, optionally halogen-substituted $C_1$- to $C_{18}$-alkyl radicals,
i has values from 1 to not more than the coordination number of the metal M,
k has values from 0 to not more than the coordination number of the metal M minus i and
l has values from 1 to 100.

8. A process for the preparation of crosslinked organopolysiloxane particles which carry metal atoms bonded chemically to the surface, as claimed in claim 1, in which, in a first step, by incorporating silanes of the general formula (12)

$$R_aSi(OR^2)_{4-a} \quad (12),$$

and, optionally, organosilicon compounds which are built up from units of the general formula (13)

$$R_b(R^2O)_cSiO_{4-b-c/2} \quad (13),$$

into an agitated mixture of emulsifier and water, a colloidal suspension of organopolysiloxane particles is prepared,
in a second step, silanes of the general formula (14)

$$AR_dSi(OR^2)_{4-d} \quad (14),$$

and/or organosilicon compounds which are built up from units of the general formula (15)

$$A_eR_f(R^2O)_gSiO_{(4-e-f-g)/2} \quad (15),$$

are added to the colloidal suspension,
with the proviso that the compounds which are built up from units of the general formula (15) contain at least one radical A and one radical (R²O),
and, in a third step, an organosilicon compound of the general formula (16)

$$(R^3R^4_2Si)_hX \quad (16),$$

is added to the colloidal suspension, with the proviso that the organosilicon compounds of the general formula (16) are water-soluble or hydrolyze in water to give a water-soluble compound,
in which
R² and R⁴ have the meanings of R,
R³ has the meanings of A or R,
X, if h=1, is —OR⁵, —ONR⁵₂ or —OOCR⁵ and if h=2, is —O— or —S—,
R⁵ has the meanings of R,
a has the values 0, 1, 2 or 3,
b and c, in each case independently of one another, have the values 0, 1, 2, 3 or 4,
d has the values 0, 1 or 2,
e, f and g, in each case independently of one another, have the values 0, 1, 2 or 3,
h has the values 1 or 2,
wherein R is identical or different monovalent SiC-bonded, optionally halogen-substituted $C_1$- to $C_{18}$-alkyl radical, and
wherein A is a ligand of the general formula $$spL' \quad (8)$$

or $$spsp'L'' \quad (9)$$

wherein sp and sp' are identical or different bivalent SiC-bonded, optionally substituted $C_1$- to $C_{18}$-hydrocarbon radicals, which can be interrupted by divalent radicals, bonded to carbon atoms on both sides, selected from the group consisting of —O—, —COO—, —OOC—, —CONR²—, —NR²CO—, —CO— and —[SiR₂]₁—.

9. A process for the preparation of crosslinked organopolysiloxane particles which carry metal atoms bonded chemically to the surface, as claimed in claim 2, in which, in a first step, by incorporating silanes of the general formula (12)

$$R_aSi(OR^2)_{4-a} \quad (12),$$

and, optionally, organosilicon compounds which are built up from units of the general formula (13)

$$R_b(R^2O)_cSiO_{4-b-c/2} \quad (13),$$

into an agitated mixture of emulsifier and water, a colloidal suspension of organopolysiloxane particles is prepared,
in a second step, silanes of the general formula (14)

$$AR_dSi(OR^2)_{4-d} \quad (14),$$

and/or organosilicon compounds which are built up from units of the general formula (15)

$$A_eR_f(R^2O)_gSiO_{(4-e-f-g)/2} \quad (15),$$

are added to the colloidal suspension, with the proviso that the compounds which are built up from units of the general formula (15) contain at least one radical A and one radical ($R^2O$), and, in a third step, an organosilicon compound of the general formula (16)

$$(R^3R^4{}_2Si)_hX \qquad (16),$$

is added to the colloidal suspension, with the proviso that the organosilicon compounds of the general formula (16) are water-soluble or hydrolyze in water to give a water-soluble compound, in which $R^2$ and $R^4$ have the meanings of R, $R^3$ has the meanings of A or R, X, if h=1, is —$OR^5$, —$ONR^5{}_2$ or —$OOCR^5$ and if h=2, is —O— or —S—, $R^5$ has the meanings of R, a has the values 0, 1, 2 or 3, b and c, in each case independently of one another, have the values 0, 1, 2, 3 or 4, d has the values 0, 1 or 2, e, f and g, in each case independently of one another, have the values 0, 1, 2 or 3, h has the values 1 or 2, wherein R is identical or different monovalent SiC-bonded, optionally halogen-substituted $C_1$- to $C_{18}$-alkyl radical, and wherein A is a ligand of the general formula $$spL' \qquad (8) \text{ or}$$

$$spsp'L'' \qquad (9)$$

wherein sp and sp' are identical or different bivalent SiC-bonded, optionally substituted $C_1$- to $C_{18}$-hydrocarbon radicals, which can be interrupted by divalent radicals, bonded to carbon atoms on both sides, selected from the group consisting of —O—, —COO—, —OOC—, —$CONR^2$—, —$NR^2CO$—, —CO— and —$[SiR_2]_1$—.

10. A process for the preparation of crosslinked organopolysiloxane particles which have metal atoms bonded chemically to the surface, as claimed in claim 3, in which, in a first step, by incorporating silanes of the general formula (12)

$$R_aSi(OR^2)_{4-a} \qquad (12),$$

and, optionally, organosilicon compounds which are built up from units of the general formula (13)

$$R_b(R^2O)_cSiO_{4-b-c/2} \qquad (13),$$

into an agitated mixture of emulsifier and water, a colloidal suspension of organopolysiloxane particles is prepared, in a second step, silanes of the general formula (14)

$$AR_dSi(OR^2)_{4-d} \qquad (14),$$

and/or organosilicon compounds which are built up from units of the general formula (15)

$$A_eR_f(R^2O)_gSiO_{(4-e-f-g)/2} \qquad (15),$$

are added to the colloidal suspension, with the proviso that the compounds which are built up from units of the general formula (15) contain at least one radical A and one radical ($R^2O$), and, in a third step, an organosilicon compound of the general formula (16)

$$(R^3R^4{}_2Si)_hX \qquad (16),$$

is added to the colloidal suspension, with the proviso that the organosilicon compounds of the general formula (16) are water-soluble or hydrolyze in water to give a water-soluble compound, in which $R^2$ and $R^4$ have the meanings of R, $R^3$ has the meanings of A or R, X, if h=1, is —$OR^5$, —$ONR^5{}_2$ or —$OOCR^5$ and if h=2, is —O— or —S—, $R^5$ has the meanings of R, a has the values 0, 1, 2 or 3, b and c, in each case independently of one another, have the values 0, 1, 2, 3 or 4, d has the values 0, 1 or 2, e, f and g, in each case independently of one another, have the values 0, 1, 2 or 3, h has the values 1 or 2, wherein R is identical or different monovalent SiC-bonded, optionally halogen-substituted $C_1$- to $C_{18}$-alkyl radical, and wherein A is a ligand of the general formula $$spL' \qquad (8) \text{ or}$$

$$spsp'L'' \qquad (9)$$

wherein sp and sp' are identical or different bivalent SiC-bonded, optionally substituted $C_1$- to $C_{18}$-hydrocarbon radicals, which can be interrupted by divalent radicals, bonded to carbon atoms on both sides, selected from the group consisting of —O—, —COO—, —OOC—, —$CONR^2$—, —$NR^2CO$—, —CO— and —$[SiR_2]_1$—.

11. A process for the preparation of crosslinked organopolysiloxane particles which carry metal atoms bonded chemically to the surface, as claimed in claim 5, in which, in a first step, by incorporating silanes of the general formula (12)

$$R_aSi(OR^2)_{4-a} \qquad (12),$$

and, optionally, organosilicon compounds which are built up from units of the general formula (13)

$$R_b(R^2O)_cSiO_{4-b-c/2} \qquad (13),$$

into an agitated mixture of emulsifier and water, a colloidal suspension of organopolysiloxane particles is prepared, in a second step, silanes of the general formula (14)

$$AR_dSi(OR^2)_{4-d} \qquad (14),$$

and/or organosilicon compounds which are built up from units of the general formula (15)

$$A_eR_f(R^2O)_gSiO_{(4-e-f-g)/2} \qquad (15),$$

are added to the colloidal suspension, with the proviso that the compounds which are built up from units of the general formula (15) contain at least one radical A and one radical ($R^2O$), and, in a third step, an organosilicon compound of the general formula (16)

$$(R^3R^4{}_2Si)_hX \quad (16),$$

is added to the colloidal suspension, with the proviso that the organosilicon compounds of the general formula (16) are water-soluble or hydrolyze in water to give a water-soluble compound, in which $R^2$ and $R^4$ have the meanings of R, $R^3$ has the meanings of A or R, X, if h=1, is —$OR^5$, —$ONR^5{}_2$ or —$OOCR^5$ and if h=2, is —O— or —S—, $R^5$ has the meanings of R, a has the values 0, 1, 2 or 3, b and c, in each case independently of one another, have the values 0, 1, 2, 3 or 4, d has the values 0, 1 or 2, e, f and g, in each case independently of one another, have the values 0, 1, 2 or 3, h has the values 1 or 2, wherein R is identical or different monovalent SiC-bonded, optionally halogen-substituted $C_1$- to $C_{18}$-alkyl radical, and wherein A is a ligand of the general formula $$spL' \quad (8) \text{ or}$$

$$spsp'L'' \quad (9)$$

wherein sp and sp' are identical or different bivalent SiC-bonded, optionally substituted $C_1$- to $C_{18}$-hydrocarbon radicals, which can be interrupted by divalent radicals, bonded to carbon atoms on both sides, selected from the group consisting of —O—, —COO—, —OOC—, —$CONR^2$—, —$NR^2CO$—, —CO— and —$[SiR_2]_1$—.

12. The process as claimed in claim 11, in which, after isolation after the third step, organopolysiloxane particles which comprise more than 15% by weight in total of units of the general formulae (6) and (7) are treated, in a fourth reaction step in an aprotic solvent, with an organosilicon compound of the general formulae (17)

$$(R^6R^7{}_2Si)_iY \quad (17),$$

or (18)

$$R^8R_2{}^9Si-Z(R^{10})_j$$
$$(CH_2)_k$$

in which $R^6$ and $R^8$ have the meanings of A or R, $R^7$, $R^9$ and $R^{10}$ have the meanings of R, Y, if i=1, is a halogen atom, —$OR^6$, —$NR^6{}_2$, —$ONR^6{}_2$ or -$OCCR^6$ and if i=2, is —O—, =$N(R^6)$ or —S—, Z, if j=1, is —N— and if j=0, is —O— or —S—, i has the values 1 or 2, j has the values 0 or 1, k has the values from 1 to 30, wherein R is identical or different monovalent SiC-bonded, optionally halogen-substituted $C_1$- to $C_{18}$-alkyl radical, and wherein A is a ligand of the general formula $$spL' \quad (8) \text{ or}$$

$$spsp'L'' \quad (9)$$

wherein sp and sp' are identical or different bivalent SiC-bonded, optionally substituted $C_1$- to $C_{18}$-hydrocarbon radicals, which can be interrupted by divalent radicals, bonded to carbon atoms on both sides, selected from the group consisting of —O—, —COO—, —OOC—, —$CONR^2$—, —$NR^2CO$—, —CO— and —$[SiR_2]_1$—.

13. The process of claim 8, wherein said first step and said second step are combined to a single step to include at least 80 mol % together of silanes of the general formulae (12), in which a has the value 2, and (14) in which d has the value 1.

14. In a catalytic process wherein one or more supported or unsupported metal compounds are employed as a catalyst, the improvement comprising selecting as at least one catalyst, a catalyst comprising the crosslinked organopolysiloxane particles carrying chemically bonded metal compounds of claim 1.

15. In a catalytic process wherein one or more supported or unsupported metal compounds are employed as a catalyst, the improvement comprising selecting as at least one catalyst, a catalyst comprising the crosslinked organopolysiloxane particles carrying chemically bonded metal compounds of claim 3.

16. In a catalytic process wherein one or more supported or unsupported metal compounds are employed as a catalyst, the improvement comprising selecting as at least one catalyst, a catalyst comprising the crosslinked organopolysiloxane particles carrying chemically bonded metal compounds of claim 5.

17. The process of claim 14 wherein said catalytic process is one selected from the group consisting of hydroformylation, hydrogenation, olefin polymerization, and hydrosilylation.

* * * * *